United States Patent
Righini

(10) Patent No.: US 11,903,824 B2
(45) Date of Patent: Feb. 20, 2024

(54) CARDIAC VALVE PROSTHESIS

(71) Applicant: Giovanni Righini, Gland (CH)

(72) Inventor: Giovanni Righini, Gland (CH)

(73) Assignee: INNOVHEART S.r.l., Milan (IT)

( * ) Notice: Subject to any disclaimer, the term of this patent is extended or adjusted under 35 U.S.C. 154(b) by 726 days.

(21) Appl. No.: 16/793,574

(22) Filed: Feb. 18, 2020

(65) Prior Publication Data

US 2020/0179113 A1 Jun. 11, 2020

Related U.S. Application Data

(62) Division of application No. 16/062,020, filed as application No. PCT/IB2016/057646 on Dec. 15, 2016.

(30) Foreign Application Priority Data

Dec. 15, 2015 (IT) .......................... 102015000083515

(51) Int. Cl.
*A61F 2/24* (2006.01)

(52) U.S. Cl.
CPC .......... *A61F 2/2418* (2013.01); *A61F 2/2412* (2013.01); *A61F 2210/0004* (2013.01); *A61F 2220/0025* (2013.01); *A61F 2250/001* (2013.01); *A61F 2250/0063* (2013.01)

(58) Field of Classification Search
CPC ......... A61F 2/24; A61F 2/2412; A61F 2/2418
See application file for complete search history.

(56) References Cited

U.S. PATENT DOCUMENTS

| | | |
|---|---|---|
| 2005/0228486 A1 | 10/2005 | Case et al. |
| 2007/0073391 A1 | 3/2007 | Bourang et al. |
| 2007/0142907 A1 | 6/2007 | Moaddeb et al. |

(Continued)

FOREIGN PATENT DOCUMENTS

| | | |
|---|---|---|
| JP | 2009-509688 A | 3/2009 |
| WO | 2008103722 A2 | 8/2008 |

(Continued)

OTHER PUBLICATIONS

International Search Report issued in Application No. PCT/IB2016/057646 dated May 11, 2017 (3 pages).

(Continued)

*Primary Examiner* — Matthew W Schall
(74) *Attorney, Agent, or Firm* — FLYNN THIEL, P.C.

(57) ABSTRACT

A prosthesis for a cardiac valve includes prosthetic leaflets which are intended to functionally replace the native leaflets of a cardiac valve following the implantation of the cardiac prosthesis. The prosthesis also includes a prosthetic member on which there are mounted the prosthetic leaflets and which is intended to take up a stable, predetermined functional configuration in which the prosthetic member and the prosthetic leaflets reproduce the functionally correct configuration for the purpose of the physiological replacement of the native cardiac valve. The prosthetic member is preconfigured so as to move gradually from an altered, temporary functional configuration, in which the prosthetic member has a deformed geometry with respect to the stable, predetermined stable functional configuration, to said stable, predetermined functional configuration.

3 Claims, 13 Drawing Sheets

(56) References Cited

U.S. PATENT DOCUMENTS

2007/0265699 A1    11/2007  Grewe et al.
2014/0222142 A1     8/2014  Kovalsky et al.
2017/0189174 A1*    7/2017  Braido .................. A61F 2/2436

FOREIGN PATENT DOCUMENTS

| WO | 2010037141 A1 | 4/2010 |
| WO | 2011002996 A2 | 1/2011 |
| WO | 2011163275 A2 | 12/2011 |
| WO | 2012063228 A1 | 5/2012 |
| WO | 2014080339 A1 | 5/2014 |
| WO | 2014105741 A1 | 7/2014 |
| WO | 2014138868 A1 | 9/2014 |
| WO | 2015118464 A1 | 8/2015 |

OTHER PUBLICATIONS

Written Opinion of the International Searching Authority issued in Application No. PCT/IB2016/057646 dated May 11, 2017 (5 pages).
International Preliminary Report on Patentability dated Feb. 16, 2018 and 408 reply thereto dated Dec. 21, 2017 both issued in Application No. PCT/IB2016/057646 (6 pages).
Notification of Transmittal of the International Preliminary Report on Patentability issued in Application No. PCT/IB2016/057646 dated Feb. 16, 2018 (1 page).
Japanese Office Action, with English translation, issued in corresponding Japanese Patent Application No. 2018-529657 dated Sep. 29, 2020 (13 pages).

* cited by examiner

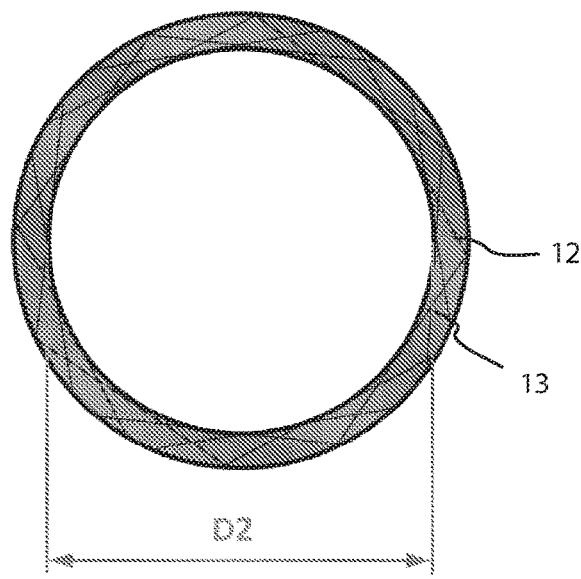
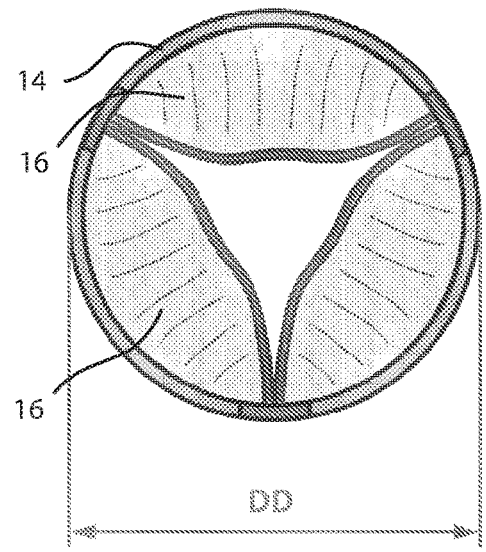
FIG.3A
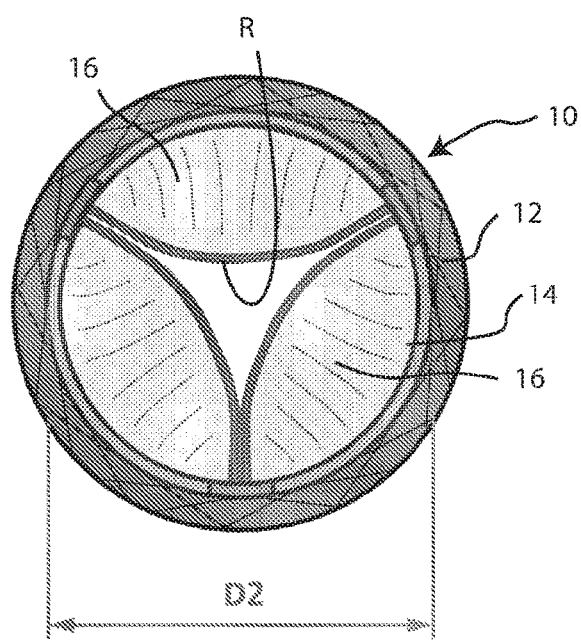
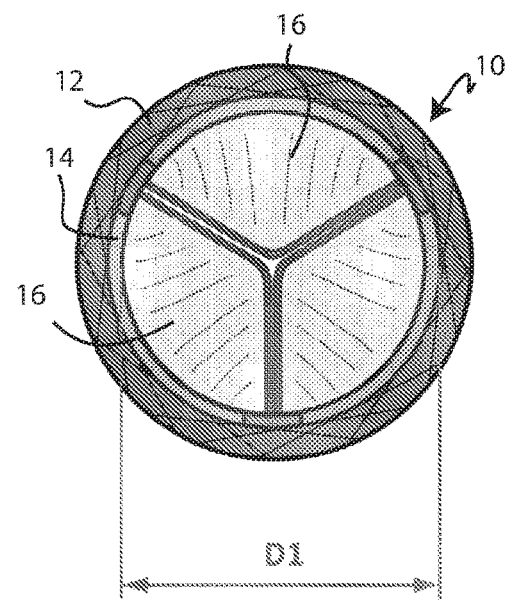
FIG.3B          FIG.3C

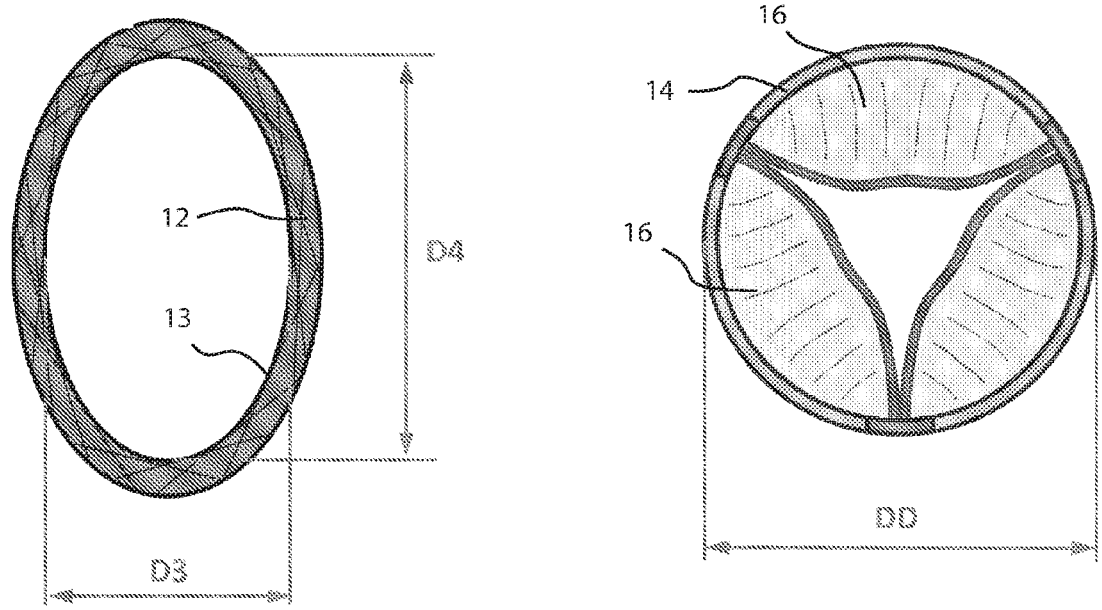
FIG.4A
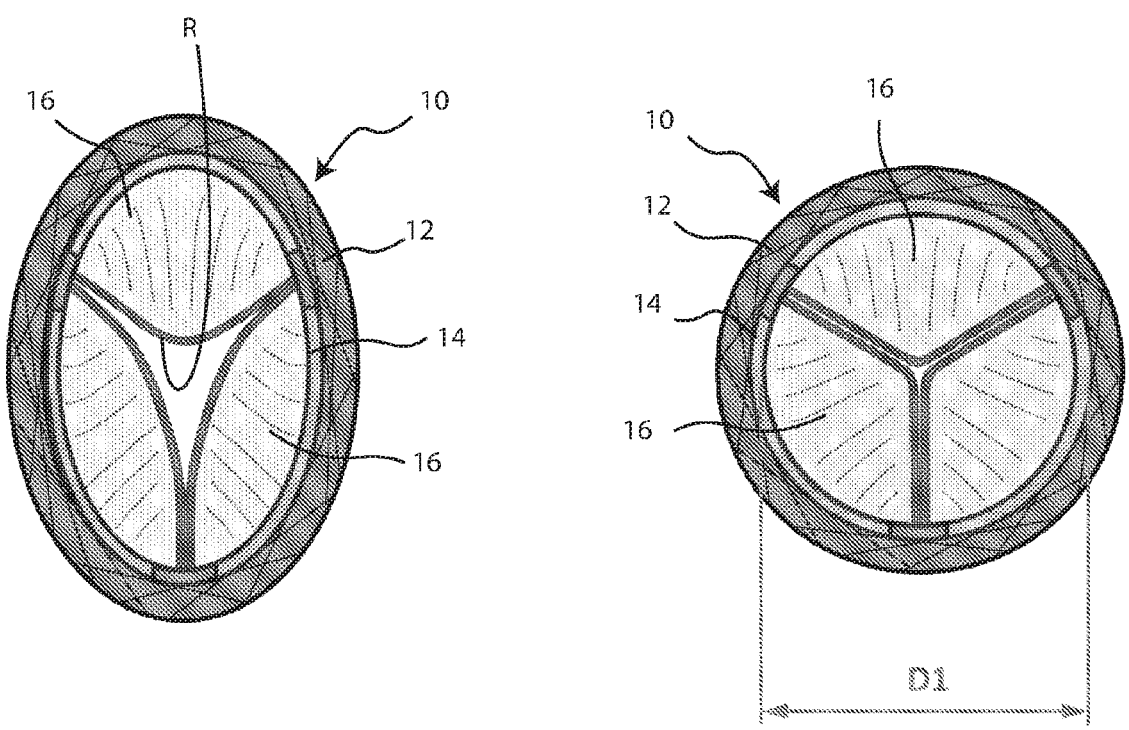
FIG.4B  FIG.4C

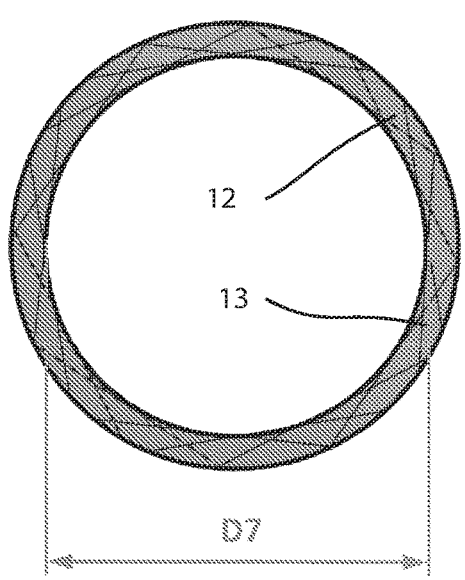
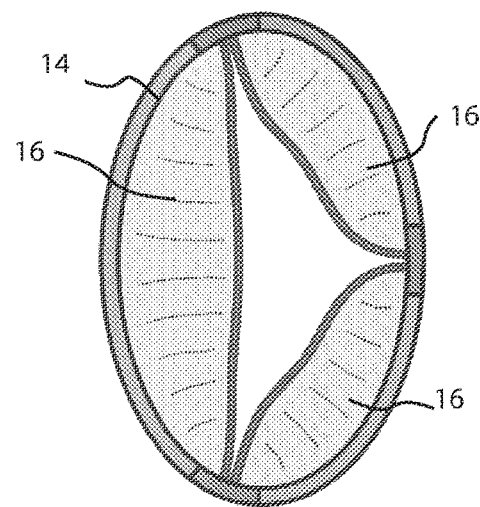
FIG.6A
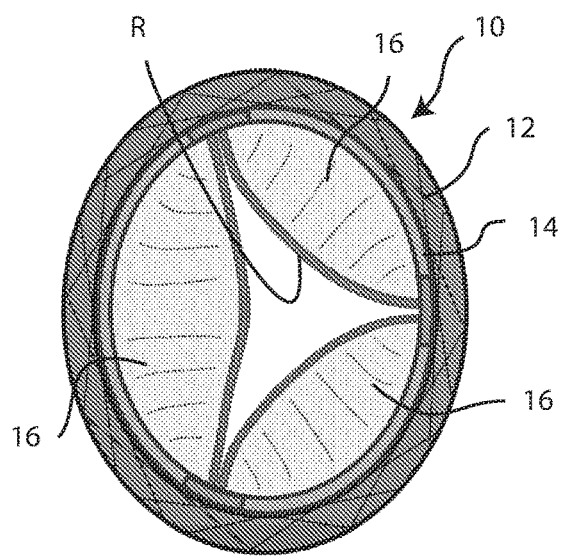
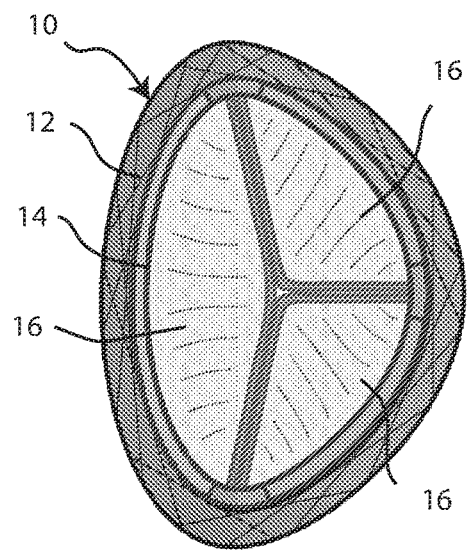
FIG.6B
FIG.6C

CARDIAC VALVE PROSTHESIS

CROSS-REFERENCE TO RELATED APPLICATIONS

This is a divisional of prior U.S. application Ser. No. 16/062 020, filed Jun. 13, 2018, which is a National Phase application of PCT Application No. PCT/IB2016/057646, filed Dec. 15, 2016, the entire contents of which is hereby incorporated herein in its entirety.

FIELD OF APPLICATION

The present invention relates to the field of implantable prosthetic devices for the treatment of malfunctions of cardiac valves.

The invention has been developed with particular regard to an implantable prosthetic device which is capable of replacing the physiological function of a malfunctioning cardiac valve.

TECHNOLOGICAL BACKGROUND

Cardiac valves are organs which preside over the correct functioning of the heart as a pump for the generation of blood flow in the circulation system of living beings. The main objective thereof involves making the blood flow unidirectional inside the cardiac cavities, being essential both in the filling phase of the cavities, known as the diastolic phase, and in the blood discharge phase, known as the systolic phase.

There are four cardiac valves which are present in the human heart. The most critical, that is to say, those whose malfunction is mainly evident as a risk of premature death or significant degradation of the quality of life, are the aortic valve and the mitral valve, both positioned at the left side of the heart, which is responsible for the peripheral vascularization of all the body. All four cardiac valves can be affected by two main malfunction types, stenosis and insufficiency, or by a combination of the two. Stenosis is defined as the pathological narrowing of the valve orifice so as to obstruct the passage of the blood through it with the valve open. Valve insufficiency or incompetence is defined, vice versa, as the incapacity of the leaflets of the valve to close completely. The incomplete coaptation of the leaflets therefore leads to the phenomenon of regurgitation, that is to say, the formation of a backward flow, with the valve closed. Stenosis of the aortic valve and insufficiency of the mitral valve are the valve pathologies which are most widespread in occidental countries.

Insufficiency of a cardiac valve is a malfunction which is hugely incapacitating for the patient and very onerous for the cardiac muscle. Insufficiency is a particularly serious malfunction for an atrio-ventricular valve, specifically for the mitral valve. That malfunction often triggers a vicious circle which leads to a rapid deterioration of the pathological outlook. In fact, blood regurgitation through the mitral valve inhibits the efficiency of the left ventricle, reducing the volume of oxygenated blood which is effectively discharged by the heart towards the peripheral chambers for the same volumetric systolic contraction of the ventricle itself. In an attempt to compensate for the reduced efficiency, the left ventricle tends to become dilated so as to increase the volume of blood pumped. However, the dilation of the ventricular chamber also results in a dilation of the annulus of the mitral valve, in addition to a deformation, and therefore malfunctioning, of the sub-valvular apparatus thereof, which tends to aggravate the lack of competence of the mitral valve itself, thereby increasing the regurgitated proportion and further reducing the pumping efficiency of the ventricle. Therefore, it is evident how the attempt to compensate for the mitral regurgitation via a dilation of the ventricle results in an increase of the regurgitation itself and therefore a triggering of a vicious circle which rapidly leads to the occurrence of cardiac insufficiency (heart failure). This outlook is further aggravated by the fact that the increase in the volume of the ventricle for diastolic purposes and the simultaneous thinning of the ventricle wall increases significantly the level of stress undergone by the cardiac muscle during the systolic phase (so-called afterload), quickly generating a state of suffering and weakening of the myocardium which contributes to the deterioration of the condition of cardiac insufficiency.

In the current state of the art, the standard therapy for the treatment of severe insufficiency of a cardiac valve is the implantation of a permanent valve prosthesis or the repair of the native valve, which method is often associated with the simultaneous implantation of devices which promote the recovery of the functionality of the valve itself, such as, for example, rings for annuloplasty, artificial tendinous cords in the case of atrio-ventricular valves, etc. In both cases, the therapy is usually applied by way of an open-heart surgical procedure which affords the cardio-surgeon direct access to the malfunctioning valve. Generally, the procedure requires the temporary arrest of the heart and the production, by means of suitable pumps and oxygen exchangers, of an artificial extra-corporeal blood circuit which is capable of extracting venous blood from the patient, oxygenating it and reintroducing it back into the arterial circulation. Notwithstanding the refinement of the techniques for controlling the cardiac arrest and the improvement in the effectiveness levels of the extra-corporeal circulation systems, the invasiveness of the open-heart treatment is a significant risk factor and the mortality associated with the surgical procedure is still high. For this reason, in many cases the general conditions of the patient, for example, the advanced age thereof or the presence of concomitant pathologies, thereby make the risks of mortality high, or of high levels of invalidity associated with the conventional surgery to be considered to be unacceptable. Therefore, the patient is refused surgical treatment, preventing access to a therapy which is essential for the resumption of the functionality of the valve and consequently the efficiency of the cardiac muscle.

In order to limit or even eliminate the risks and the disadvantages of the surgical procedure, innovative procedures for implantation with low invasiveness have recently been developed as alternatives to the conventional surgical therapies.

Initially, the reduction of invasiveness has been sought by reducing the dimensions of the surgical aperture for access to the cardiac valve with the use of prostheses which do not require stitching at the implantation site (so-called sutureless valve prostheses) and with the use of surgical instruments which are compatible with endoscopic type procedures.

More recently, there have been developed valve prostheses which are radially collapsible and which can be implanted by means of low-profile catheters which are capable of navigating inside the vascular system and of releasing the prosthetic device by reaching the implantation site by remote access. This new technology has made it possible to carry out the implantation of the replacement valve prosthesis with the heart beating, that is to say, without any need for cardiac arrest and extra-corporeal blood circulation.

Independently of the procedure followed, whether it be a surgical or transcatheter procedure, the sudden elimination of the regurgitation of an atrio-ventricular valve, as obtained following a corrective procedure or replacement, involves a specific risk as a result of the similarly sudden increase of the haemo-dynamic load undergone by the ventricle during the systolic discharge phase. Taking, for example, for the sake of simplicity of exposition, the mitral valve, a significant regurgitation in the atrium via the incompetent mitral valve reduces the haemo-dynamic load undergone by the left ventricle during the systolic discharge, it being the atrium directly connected to the pulmonary circulation and therefore characterized by low pressure systems. An effective correction of the mitral incompetence, with the total elimination of the reflux in the atrium, therefore brings about a sudden increase in the load undergone by the ventricle and therefore an abrupt increase in the force applied to the cardiac muscle. In the presence of haemo-dynamic conditions which are already critical and/or involve a dilated ventricle, this sudden overloading of the myocardial muscle may be the cause of serious acute post-procedural complications.

Another set of problems which is specifically associated with the replacement of the incompetent mitral valve with an implantable valve prosthesis via the transcatheter route and more generally with valve prostheses which do not require the production of surgical sutures at the implantation site, results from the expansion of the dimensions of the annulus of the mitral valve which is a consequence of the dilation of the cardiac chambers at the left-hand side of the heart caused by the mitral regurgitation according to the mechanism described above. Most known mitral valve prostheses of the transcatheter type are based on the expansion of a central element inside the valve opening. The main body of the prosthesis during the implantation moves from a compressed configuration which is necessary for the introduction and positioning of the prosthesis to an expanded configuration which is intended to produce continuity with the native mitral annulus. Only contact with or at least proximity to the native annulus ensures the correct functioning of the prosthesis, that is to say, suitable securing and para-valvular tightness with respect to backward flow.

Examples of transcatheter prostheses for a mitral valve which require under operating conditions radial dimensions which are congruent with respect to those of the valve annulus are described in the documents WO 2011/163275, WO 2010/037141 and WO 2011/002996, wherein a pair of circumferential rings of hooks in the first two documents and of loops in the third document, respectively, produce a mechanism for engagement with the annulus of the mitral valve. Other sets of inventive solutions which also require adaptation of the dimensions of the prostheses to the dimensions of the native annulus are described in WO 2008/103722, wherein a series of points and hooks are intended to become engaged both with the annulus and with the leaflets of the native valve, or in WO 2014/138868, wherein the central member is even shaped in a "D"-like manner in order to better fit the shape and dimensions of the mitral annulus.

It is worth underlining here how, in general, in the prior art it is the dimensions of the prosthesis which have to be adapted to the dimensions of the dilated annulus, which necessity places a great limitation on the minimum profile to which the prosthesis itself can be collapsed in the positioning and release catheter. A set of mitral valve prostheses of the sutureless type provided with a structure which interacts directly with the annulus of the mitral valve is described in the document WO 2014/080339. This document describes implantable prosthesis systems which include an annular element which is positioned at the level of the annulus so as to completely surround the native valve leaflets. The expansion inside the opening of a substantially cylindrical valve member until it is brought into contact with the above-mentioned annular element allows stabilization of the annulus, because the native leaflets remain fixed in position between the two components of the prosthetic system near the insertion line thereof in the annulus itself. This known solution, unlike the other designs described above, has the characteristic of securing in a stable manner the annulus of the native valve to itself.

STATEMENT OF INVENTION

An object of the present invention is to solve the problems of the prior art. It should be noted that it is of great use and benefit for a patient affected by valve insufficiency to provide an implantable replacement prosthesis, in particular if it is of the sutureless type, advantageously capable of bringing about in a gradual manner over time the elimination of the valve regurgitation. The prosthesis which is described below is also directed towards the production of an inverse remodelling action, that is to say, a constrictive action for reducing the dimensions, of the native valve annulus dilated by the cardiac pathology. Inter alia, the possibility of applying such inverse remodelling of the annulus would also allow the simultaneous reduction of the dimensions of the prosthesis itself, overcoming one of the disadvantages of the prior art.

Therefore, an object of the invention is to correct the pathological regurgitation of a cardiac valve, in particular an atrio-ventricular valve, having the object of complete elimination of the valve insufficiency according to a gradual transition over time, which allows better adaptation of the muscle of the ventricular wall to the new working conditions and therefore the reduction of the incidence of some complications directly associated with the valve replacement. Another object of the invention is to provide a mechanism which makes the implantable valve prosthesis capable of applying a corrective action to the anatomy of the malfunctioning native valve, combating the degenerative and dilative effects of the pathology.

Some aspects of the solution according to specific embodiments of the invention are described, for the sake of clarity of description, with reference to the prosthetic system illustrated in the patent document WO 2014/080339, the content of which is incorporated herein by reference. However, it is evident that in general terms the invention may also be applied to valve prostheses having a different configuration from that described in this patent document and that they are adapted to the treatment of the insufficiency of any cardiac valve, independently of the position thereof. In fact, any prosthetic system which includes a structure or a group of structures capable of being connected in a secure manner to the annulus of the cardiac valve to be treated may benefit from the adoption of the present invention. In particular, though not exclusively, the invention may be applied to valve prostheses having the characteristics described in the patent documents WO 2012/063228 and WO 2015/118464, the content of which is also incorporated herein.

According to a first aspect of the invention, a prosthesis for a cardiac valve comprises prosthetic leaflets which are intended to functionally replace the native leaflets of a cardiac valve following the implantation of the cardiac prosthesis, and further comprises a prosthetic member on which there are mounted the prosthetic leaflets and which is intended to take up a stable, predetermined functional configuration in which the prosthetic member and the prosthetic leaflets reproduce the functionally correct configuration for the purpose of the physiological replacement of the native cardiac valve. The prosthetic member is preconfigured so as to be fixed in an altered temporary functional configuration, in which the prosthetic member has a deformed geometry with respect to the above-mentioned stable, predetermined functional configuration. The prosthetic member is preconfigured so as to move gradually during use from the altered temporary functional configuration to the stable, predetermined functional configuration.

Advantageously, the gradual change of the prosthetic member from the altered temporary functional configuration to the stable, predetermined functional configuration can be carried out by resilient return.

According to a specific aspect, the prosthesis for a cardiac valve may comprise retention members of the prosthetic member in the altered temporary functional configuration. Those retention members are provided for gradual dissolution after the implantation of the cardiac prosthesis so as to allow the change of the prosthetic member from the altered temporary functional configuration to the stable, predetermined functional configuration. Advantageously, the retention members may be of bio-erodible or biodegradable material.

According to a specific aspect, the prosthetic member may comprise a main support member for the prosthetic leaflets and an annular peripheral abutment member which is capable of surrounding the main support member and against which the main support member can expand with such a radial force as to trap during use the native leaflets of the cardiac valve between it and the annular member. Advantageously, the annular abutment member can move from an altered temporary configuration to a stable, predetermined configuration and is provided to entrain with it the main support member of the prosthetic leaflets in order to generally define the corresponding configurations, an altered temporary functional configuration and a stable, predetermined functional configuration, of the prosthetic member as a whole, respectively. Advantageously, the annular abutment member in the altered temporary configuration can be resiliently deformed and/or extended with respect to the stable, predetermined configuration thereof. According to a specific aspect, the annular abutment member can be resiliently retained in the altered temporary configuration by the above-mentioned retention members. Advantageously, the retention members can be inserted into cavities of the annular abutment member. According to a variant, the retention members may comprise a matrix, in which at least a portion of the core of the annular abutment member is incorporated.

According to a specific aspect, the deformation of the annular abutment member in the altered temporary configuration may be anisotropic. Advantageously, the annular abutment member may comprise at least one continuous ring in order to make the annular member deformable and inextensible. Advantageously, the annular abutment member may comprise at least two continuous rings which are axially spaced apart in order to make the annular member deformable only in the plane of the annular abutment member.

According to a specific aspect, the cardiac prosthesis is generally collapsible in a non-functional configuration with a small spatial requirement which is capable of implantation by means of techniques of the transcatheter type.

The invention also relates to a method for producing a prosthesis for a cardiac valve. That method advantageously comprises the steps of:

providing a prosthesis for a cardiac valve comprising prosthetic leaflets which are intended to functionally replace the native leaflets of a cardiac valve following the implantation of the cardiac prosthesis, and a prosthetic member on which there are mounted the prosthetic leaflets and which is intended to take up a stable, predetermined functional configuration in which the prosthetic member and the prosthetic leaflets reproduce the functionally correct configuration for the purpose of the physiological replacement of the native cardiac valve, geometrically deforming the prosthetic member and fixing it in such a manner that it takes up an altered temporary functional configuration with a deformed geometry with respect to the stable, predetermined configuration, preconfiguring it in such a manner that it can move gradually during use from the altered temporary functional configuration to the stable, predetermined functional configuration.

According to a specific aspect of the above-mentioned method, the prosthetic member may be resiliently deformed geometrically and fixed in the altered temporary functional configuration by means of retention members which are gradually dissolvable during use.

In general terms, the solution in accordance with one or more embodiments of the invention is based on the operation of deforming, preferably in a resilient range before implantation, the structure which is mechanically connected to the valve annulus and stabilizing that deformed configuration in a temporary manner so that the deformation interferes with the behaviour of the prosthesis for a predetermined but limited period of time following the implantation of the prosthesis. The deformed configuration of the structure has to be such as to bring about the partial incompetence of the prosthetic device. For an atrio-ventricular valve, for example, the prosthetic system has, for a limited period of time immediately after the implantation, a predefined degree of incompetence, that is to say, of intra-prosthetic regurgitation, capable of partializing the sudden increase of the systolic load undergone by the ventricle associated with the elimination of the valve insufficiency. Once a given period of time has elapsed, possibly determined, at least in principle, at the design stage, the preferably resilient return of the material which composes the annular element brings about the recovery of the correct geometry thereof and the elimination of the anomalous deformation imposed on the prosthetic device. This last effect therefore involves the disappearance of the incompetence of the prosthetic leaflets and the intra-prosthetic valve regurgitation.

In addition to the above-mentioned effect, the deformation which is temporarily imposed may bring about an increase in the dimensions of the portion of the structure which during the implantation method carries out the connection to the native annulus and interacts therewith. In this manner, the structure and therefore the entire prosthetic system are suitable for being implanted in an annulus having dimensions greater than those which would be compatible with the same prosthetic system but having the structure without the deformation imposed.

Downstream of the implantation method, in a period of time which may be from a few days up to several weeks, the constraint which brings about the deformation imposed on the structure gradually dissolves, allowing the recovery of the true geometry and/or the dimensions of the structure, and therefore the entire prosthetic system, in the implantation system. The disappearance of the constraint for deforming the structure cancels the incompetence of the valve prosthesis together with a reduction of the dimensions of the valve annulus. There is thereby obtained the elimination of the valve insufficiency in a gradual manner, with a less traumatic effect on the myocardial muscle, and an inverse remodelling of the annulus of the native valve.

It is evident that the two functional properties described above, that is to say, the capacity for making the correction of the valve regurgitation gradual and the capacity for reducing the dimensions of the annulus, do not necessarily have to be both present at the same time. As will be described below, in fact, it is possible to produce the gradual nature of the correction of the insufficiency without necessarily producing the inverse remodelling of the annulus. This behaviour may be required if the dilation of the valve annulus is not clinically appreciable.

More specifically, a solution in accordance with an embodiment of the invention is compatible with a prosthetic system which comprises an annular element which is capable of being positioned at the rear of the leaflets of the native intra-ventricular valve, so as to surround it completely, and a central valve member which is collapsible to a diameter which is substantially less than that of the implant and which is capable of expanding inside the mitral opening. This solution makes provision for the annular element which is part of the prosthetic system to include a core which is generally but not necessarily produced from metal material which has in toto or even only partially a meshed form, or a helical form, or any geometry which allows the resilient deformation thereof both in extension, that is to say, in the longitudinal direction (obtaining the increase of the axial extent of the annular element, that is to say, the overall length), and with respect to the plane in which the annular element is located, that is to say, in a transverse direction (obtaining the variation of shape of the annular element). During the construction step of the component, the structure is deformed in accordance with degrees of freedom which are allowed by the configuration thereof and in any case not beyond the resilience limit of the material from which it is composed, in order to ensure the resilient return thereof to the natural configuration once the constraint which maintains it in the deformed configuration is removed. By way of example, the annular element may be deformed by increasing the axial extent thereof or by imposing an ovalized geometry or in any case a geometry which is different from the one expected during the normal operation condition, or by applying the two deformations at the same time. An annular element modified in this manner achieves the double result both of making the prosthetic system suitable for the implantation in a native annulus having greater dimensions, as a result of the increased circumferential extent and therefore the equivalent diameter of the annular element, and of bringing about the intra-prosthetic insufficiency in the implanted device. With regard to this last point, it may be observed that the central member of the prosthetic system, which element supports the prosthetic leaflets, is preferably constituted by a collapsible and expansible frame, the expanded formation of which, once the prosthesis is implanted, is limited by the geometry, the dimensions and the resilient characteristics of the annular element which completely surrounds it. In fact, during the implantation method, the central member expands until it is mechanically connected to the annular element. The final configuration of the prosthesis is therefore determined by the result of the balance between the radial force applied by the central member, the expansion of which remains limited and incomplete in any case, and the constraint constituted by the annular element. The prosthetic leaflets which are supported by the central member have dimensions adapted to provide optimum coaptation and therefore effective fluid-tightness with respect to the intra-prosthetic regurgitation, at the expected final configuration of the implant. By imposing an additional deformation on the annular element, as mentioned above, the final formation of the central member is consequently modified, thereby being over-expanded or ovalized, or at any rate having a form different from that expected under normal operating conditions, or as a result of the combination of the two deformations. As a final effect, the prosthetic leaflets are not connected to each other in an optimum manner and are incompetent, and the valve prosthesis exhibits intra-prosthesis regurgitation.

In solutions in accordance with the embodiments of the present invention, the deformed configuration of the annular element is fixed by supplying material which is characterized by erodible or degradable properties in contact with blood and/or under the physiological conditions of the human body. By way of an application example, without wishing to limit in any way the general nature of the invention, it is possible to obtain the result of fixing the deformation of the annular element by supplying bio-erodible material which suitably fills the cavities of the mesh or the helix which constitutes the core thereof, in accordance with the configuration adopted, or by covering completely, or only suitable portions of, the structural elements of the core, and therefore stiffening it in the deformed configuration thereof. Once the prosthesis is implanted, the bio-erodible material which is added for fixing the deformed configuration of the annular element comes into contact with the haematic fluid and begins the process of degradation thereof. This bio-erosion results in a progressive reduction of the capacity of the filler material to interfere with the annular element which similarly therefore gradually recovers a configuration of resilient equilibrium only with the central member, without any superimposition of a deforming effect as a result of the filler material. By way of example, if there have been applied both the above-described deformations to the annular element, it begins to reduce the circumferential extent thereof, producing an action involving inverse remodelling, that is to say, contraction, of the native mitral annulus and at the same time allows a recovery of the circularity of the central member. The two combined effects return the intended coaptation to the prosthetic valve leaflets, eliminating the intra-prosthesis regurgitation which is exhibited by the device during the acute post-implantation period.

The rate of degradation of the bio-erodible filler material may be sufficiently predetermined by way of the chemical composition and the physical characteristics of the material itself. In this manner, it is possible to adjust the time required for the prosthesis to recover the configuration thereof which is functionally stable during operation. It is thereby possible to establish a priori the transient period over which the left ventricle recovers full haemodynamic load which is associated with the total elimination of the mitral insufficiency.

In solutions according to one or more embodiments of the present invention, the core of the annular element may be produced from any biocompatible metal alloy, such as, for example, titanium alloys, which are already characterized by a wide clinical experience in similar applications. However, it appears to be advantageous, under general consideration of the necessary functional requirements required by the sutureless implantation technologies and even more so by transcatheter implantation technologies, to use super-resilient alloys, that is to say, those which allow great deformations while remaining in a resilient range, that is to say, without being subjected to permanent distortions. An example of a super-resilient alloy already in use for sutureless and transcatheter valve prostheses is the nickel-titanium alloy which has equal atomic percentages and which is commercially known under the name Nitinol.

With regard to the fixing material for the deformed configuration of the annular element, in the current prior art there are known various materials of the bio-erodible or biodegradable type, that is to say, biocompatible materials which are capable of being degraded under the physiological conditions of the human body and in contact with the haematic flow. Examples of materials with those characteristics are polymers based on polylactic acid, polydioxanone acid (PDS), polyglycolic acid (PGA) or the copolymers thereof, wherein the addition of other monomers, such as, for example, lactic acid or trimethylene carbonate, allows adjustment of the degradation and solubility rate in accordance with the relationship between the various monomers used in the synthesis and the nature itself of those monomers. Those polymers are available in various forms which allow different types of use for the purposes of the present invention. For example, polyglycolic acid is already used for producing surgical suture threads which can be re-absorbed. In embodiments of the present invention, there are provided re-absorbable threads which can be wrapped about the core of the deformed annular element so as to fill, for example, the cavities thereof present in the configuration of the structure, thereby temporarily preventing the resilient return thereof and actually fixing it in position in the altered or deformed temporary configuration. There are also known bio-erodible materials which are used to produce biodegradable medical devices which can be implanted, such as screws, plates, etc. Those materials can be used in the present invention in order to produce members such as inserts, wedges and the like, which are shaped so as to fill the cavities of the core of the annular element, thereby securing it in the altered or deformed temporary configuration. In other embodiments of the present invention, the bio-erodible material may form a matrix in which at least a portion of the core of the annular element can be incorporated so as to be retained in the altered or deformed configuration. In many cases, in fact, bio-erodible polymers have good mechanical characteristics: PGA fibres, for example, are characterized by a value of Young's modulus of approximately 7 GPa, that is to say, ten times greater, for example, than high-density polyethylene (HDPE).

In the scope of the various embodiments of the present invention, the deformation or alteration temporarily imposed on the annular element in order to achieve the advantages described above may also apply only to single portions of the annular element itself and the entire structure thereof. Similarly, the present invention may also be applied according to the same principles to annular structures which are subdivided into a plurality of segments which are physically separated from each other.

BRIEF DESCRIPTION OF THE DRAWINGS

The solution in accordance with one or more embodiments of the invention, as for other characteristics and the relevant advantages, will be better appreciated with reference to the following detailed description which is given purely by way of non-limiting example and which is intended to be read together with the appended Figures, in which for simplicity corresponding elements are indicated with identical or similar reference numerals and the explanation thereof is not repeated. In this regard, it should be expressly understood that the Figures are not necessarily drawn to scale (with some details which can be exaggerated and/or simplified) and that unless indicated otherwise they are simply used to conceptually illustrate the structures and methods described. In particular in the drawings:

FIGS. 2A, 2B show as a perspective view and plan view the two components of the prosthesis illustrated in FIG. 1A and 1B, respectively;

FIGS. 3A, 3B and 3C describe the same components of the prosthetic device both in the separated and in the assembled configuration, wherein it is assumed that the annular element is temporarily deformed in the direction increasing the circumferential extent thereof longitudinally, with the recovery of the correct operational configuration once the cause of the deformation has been eliminated;

FIGS. 4A, 4B and 4C describe the same components of the prosthetic device both in the separated and in the assembled configuration, wherein it is assumed that the annular element is temporarily deformed in the direction of ovalization of the shape, with the recovery of the correct operational configuration once the cause of the deformation has been eliminated;

FIGS. 6A, 6B and 6C show the same components of the prosthetic device described in FIGS. 5A, 5B and 5C, both in the separated and in the assembled configuration, wherein it is assumed that the annular element is temporarily deformed both by increasing the circumferential extent thereof and by varying the shape thereof, with the recovery of the correct operational configuration once the cause of the deformation has been eliminated;

DETAILED DESCRIPTION OF PREFERRED EMBODIMENTS

Figure 1A:
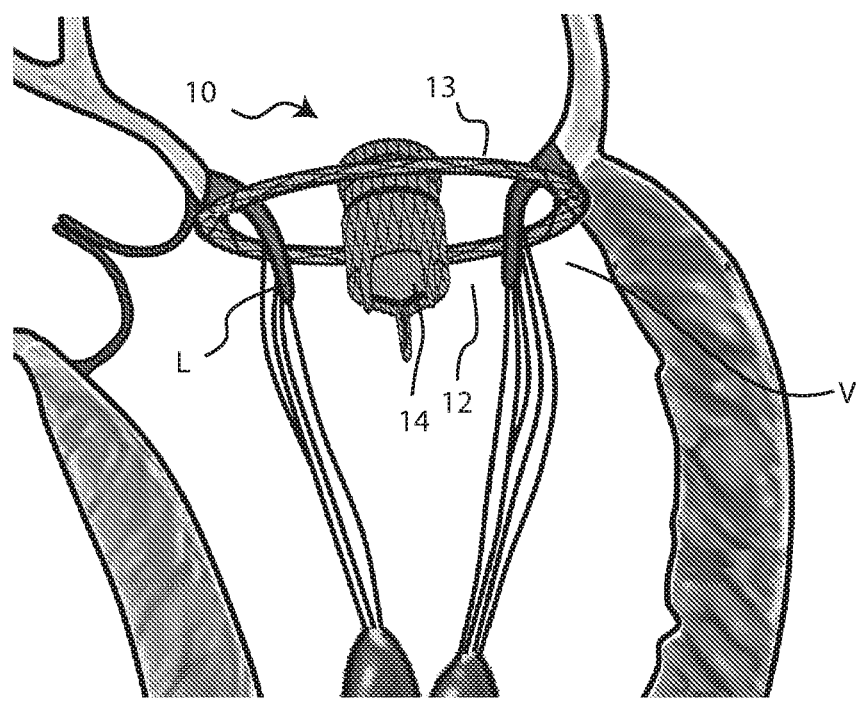
FIGS. 1A and 1B show in configurations corresponding to different steps of the implantation method general schematic representations of a prosthetic device for the treatment of cardiac valves, in accordance with a configuration compatible with the embodiments of the present invention.
Figure 1B:
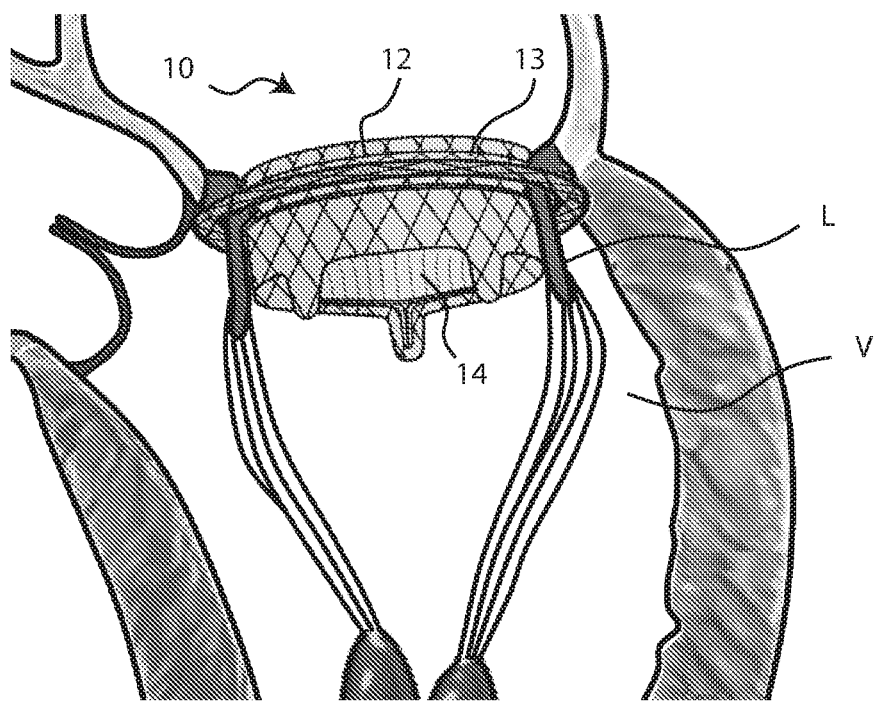

FIGS. 1A and 1B schematically illustrate two different steps of the implantation method of a prosthesis 10 for a cardiac valve according to the present invention, which prosthesis is used to replace the functionality of a native atrio-ventricular valve V to be treated. The prosthesis 10 comprises a first component in the form of an annular element 12 and a second component in the form of a central member 14, which supports prosthetic valve leaflets 16. During the implantation method, the annular element 12 is positioned outside the native atrio-ventricular valve V in order to completely surround it, while the central member 14 is expanded inside the same native atrio-ventricular valve V (FIG. 1A). The expansion of the central member 14 causes the two components 12, 14 to be connected to each other (FIG. 1B). The contact between the two components 12, 14 is not direct but instead occurs with the interposition of the leaflets L of the native valve V which remain interpolated between the two components 12, 14. As a result of the flexibility and deformability of the native atrio-ventricular valve V, the final configuration of the prosthesis 10 is determined mainly by the balance of the mutually exchanged forces during the interaction between the two components 12, 14 and is a function of the resilient return of each of the two components 12, 14. In particular, if the annular element 12 is substantially inextensible or at least mainly rigid in a circumferential direction, that is to say, in the longitudinal direction, with respect to the exchanged forces, the central member 14 expands as far as the radial dimension allowed by the length of the internal circumference 12a of the annular element 12. The configuration of final equilibrium, that is to say, post-implantation, of the prosthesis 10 is therefore predictable and controllable, because the contribution of the native valve in terms of structural interaction is substantially negligible. The diagram described in FIGS. 1A and 1B is purely indicative of the principle of basic operation of the prosthesis 10, and in the context of that construction solution there can be provided different solutions. For example, the annular element 12 can be open and/or subdivided into a plurality of portions in order to allow ready positioning thereof around the native atrio-ventricular valve V.

The annular element 12 is then re-closed and/or re-assembled before the expansion of the central member 14. There can further be provided flexible arms for connection between the annular element 12 and the central member 14 in order to keep the mutual positioning stable and predefined between the two components 12, 14 during the implantation steps of the prosthesis 10. Furthermore, the final configuration of the prosthesis 10 may provide for a circular or oval or D-like opening in accordance with the requirements of the configuration considered, for example, to reproduce a general geometry which is mainly similar to the native atrio-ventricular valve V.

Figure 2B:
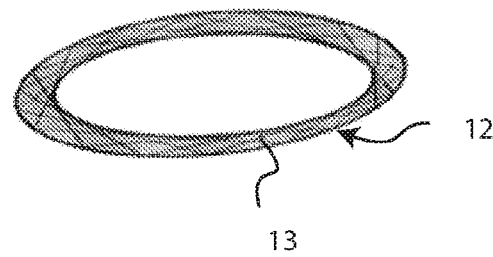
Figure 2B:
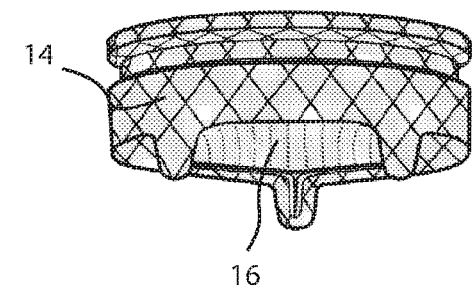
Figure 2B:
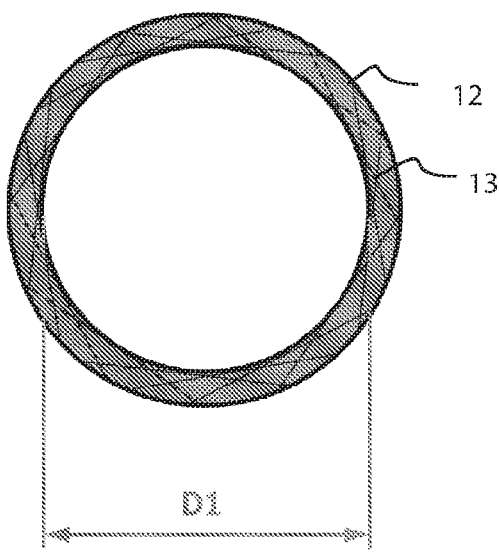
Figure 2B:
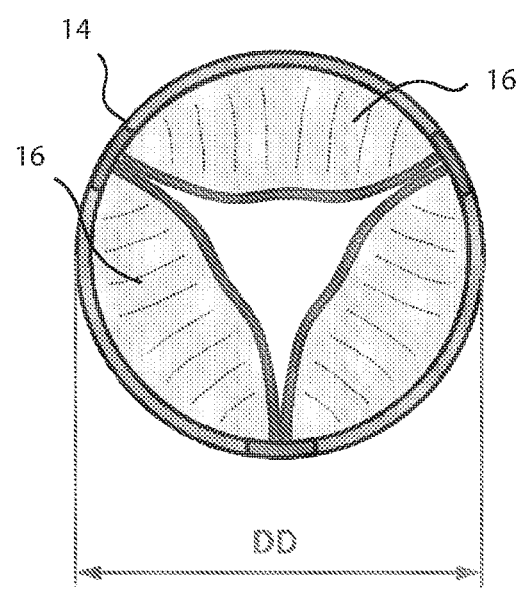
Figure 2C:
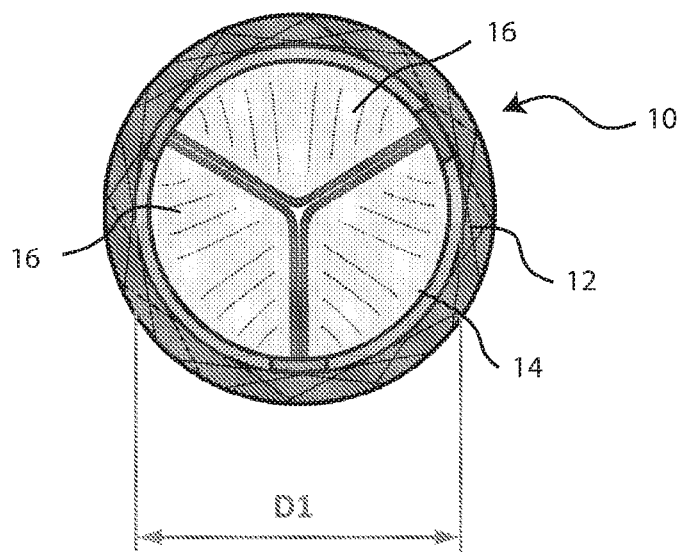
FIG. 2C shows the assembled configuration of the components of FIGS. 2A and 2B.

FIGS. 2A, 2B and 2C schematically illustrate examples of the two main components 12, 14 of the prosthesis 10. Different configurations of the components or the prosthetic system as a whole do not influence the applicability and the efficiency of the present invention and the construction solutions thereof described herein below. In particular, FIG. 2A shows perspective views of the annular element 12, in the left of the Figure, and the central member 14, on the right of the Figure. FIG. 2B illustrates the same two components 12, 14 as a plan view, in which there can clearly be seen the prosthetic valve leaflets 16 which are supported by the central member 14.

With reference to FIG. 2B, the internal diameter D1 of the annular element 12 is less than the external diameter DD of the central member 14 at the maximum expansion thereof, that is to say, in the absence of any external constraint, measured at the cross-section at which the two components are mechanically connected together. The interference which exists between the internal diameter D1 of the annular element 12 is less than the external diameter DD of the central member 14, causing during use the radial expansion of the central member 14 to be stopped against the constituted constraint of the annular element 12, generating a contact pressure which is substantially continuous over all the contact surface between the two components 12, 14 so as to make the connection thereof stable and at the same time blocking the native leaflets V, which are interpolated between the two components 12, 14 in a functionally stable configuration of the prosthesis 10. The prosthetic valve leaflets 16 which are supported inside the central member 14 are dimensioned so as to have in the functionally stable configuration of the prosthesis 10 optimum mutual coaptation. In the functionally stable configuration of the prosthesis 10, that is to say, when the central member 14 is expanded as far as the diameter and in the configurations which are determined by the radial constraint produced by the annular element 12 which surrounds it, the prosthetic valve leaflets 16 have the capacity for completely sealing the opening of the prosthesis 10 during closure in order to eliminate any backward flow, as shown schematically in FIG. 2C, which illustrates as a plan view the two components 12, 14 in the characteristic assembled configuration of the implanted prosthesis 10.

In the configuration of maximum possible expansion of the main member 14, as can be seen on the right in FIG. 2B, the prosthetic valve leaflets 16 are incompetent and therefore the closure of the valve is insufficient. According to an aspect of the present invention, the central member 14 is allowed to expand to a greater extent and/or in accordance with a different geometry from that provided for in the functionally stable configuration of FIG. 2C so that the coaptation between the prosthetic valve leaflets 16 is intentionally partial and in any case insufficient over a transient time period. Therefore, the prosthesis 10 is affected during the operation thereof under those temporary conditions which are altered with respect to the functionally stable configuration by a degree of intra-prosthetic incompetence, that is to say, by a backward flow through the opening, proportional to the whole of the deformation to which the central member 14 is subjected with respect to the functionally stable configuration thereof, that is to say, with respect to the optimum operating condition.

FIGS. 3A, 3B and 3C show the prosthesis 10 in which the annular element 12 has at least for a limited period of time an internal diameter D2 which is dimensionally intermediate between the internal diameter D1 which is capable of retaining the central member 14 in the functionally stable configuration and the external diameter DD which the same completely expanded central member 14 would assume without any external constraint. As illustrated in FIG. 3B, the assembled prosthesis 10 has an expansion of the central member 14 which is limited by the annular element 12 which winds round it, with the two components 12, 14 connected to each other at a diameter of equilibrium which is greater than the optimum one of the functionally stable configuration as in FIG. 2C. Consequently, the coaptation during closure between the prosthetic valve leaflets 16 is also insufficient (FIG. 3B) and a central regurgitation opening R remains present inside the aperture with the valve closed. The pre-dilation of the annular element 12 to a circumferential extent greater than that provided for by the optimum connection between the two components 12, 14 determines the loss of sealing capacity with inverse flow at the side of the prosthesis 10, which is therefore incompetent. If the deformation of the annular element 12 were permanent, the prosthesis 10 would be stably incompetent in terms of the in-vivo operation thereof. If, however, the annular element 12 is capable of gradually recovering the longitudinal elongation thereof over time, over a similar transient period the regurgitation will also tend to decrease as far as being eliminated. At the end of this transient period, the valve prosthesis 10 will acquire full competence with respect to inverse flow during in-vivo operation thereof in accordance with the optimum configuration thereof, which is functionally stable illustrated in FIG. 3C.

FIGS. 4A, 4B and 4C illustrate a prosthesis 10 in which the annular element 12 assumes at least for a limited period of time a geometric shape which is different from the one provided for functionally suitable stable operation of the implanted prosthesis 10. The example set out in FIG. 4A, shows, with simple non-limiting explanatory purpose of the general nature of the invention, the annular element 12 which is deformed to an ovalized geometry with a smaller diameter D3 and greater diameter D4. Generally, the internal circumference 12a of the annular element 12 has a length equivalent to the circumference of the diameter D1 of FIGS. 2A and 2B. In other words, the annular element 12 shown in FIG. 4A is substantially obtained by means of ovalization of the annular element 12 which is shown in FIGS. 2A and 2B. In general, it is possible to impose a deformation which is also different from the oval shape, as will be shown below. The result of the deformation of the annular element 12 is schematically shown in FIG. 4B, wherein the assembled system which represents the implanted configuration of the prosthesis 10 also shows an ovalization of the central member 14 with a resultant distortion of the prosthetic valve leaflets 16 and loss of the coaptation during closure. The deformation in terms of shape of the annular element 12 therefore allows the solid connection between the two components 12, 14 of the prosthesis 10, but does not bring about at the same time the incompetent closure, with the appearance of intra-prosthesis regurgitation. In that case too, if the deformation in terms of shape is temporary, that is to say, if the annular element 12 is capable of recovering over time the functionally correct shape thereof, the prosthesis 10 as a whole will also gradually recover the appropriate closure of the prosthetic valve leaflets 16, being completely competent at the end of the transient period, as indicated in FIG. 4C.

The alterations of length and shape of the annular element 12 described above with reference to FIGS. 3A and 4A may also be applied simultaneously, resulting in a combination of an increase in the circumferential extent of the annular element 12 and a variation in terms of shape thereof. Via this combination of deformations, which are temporary and reversible according to the techniques already described above, there is obtained at the same time the corrective constriction effect, that is to say, of inverse remodelling, of the dilated annulus of the native pathological atrio-ventricular valve V, to which the annular element 12 is connected during the implantation step, and the temporary incompetence effect of the prosthesis 10, which advantageously allows a risky sudden increase of the haemodynamic load undergone by the ventricular muscle immediately after the prosthesis 10 is implanted to be prevented.

Figure 5A:
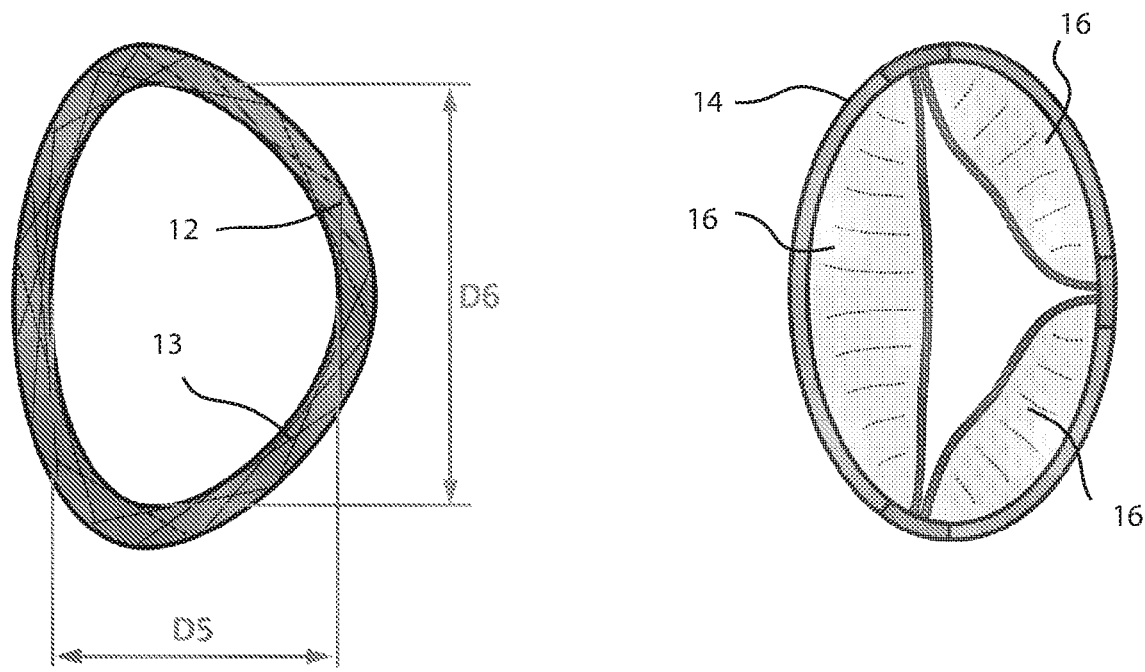
FIGS. 5A and 5B show another version of the components of the prosthetic device which is for the treatment of cardiac valves and which is described in FIGS. 1A and 1B, both in the separated and in the assembled configuration, having different geometries from a circular geometry.
Figure 5B:
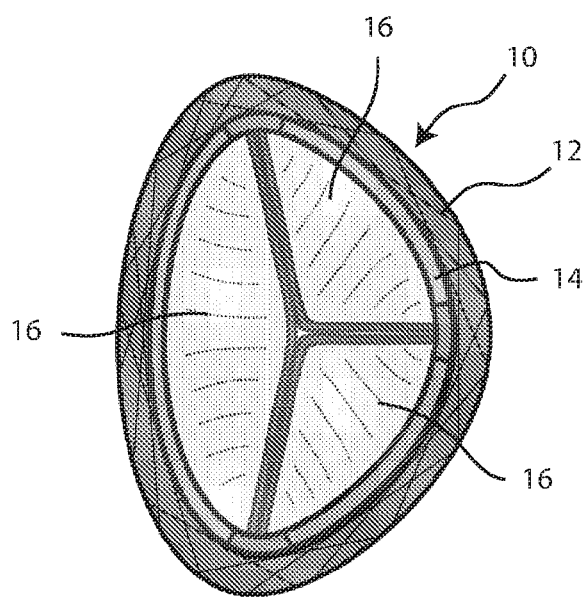

The examples set out in the preceding Figures are purely indicative and are not intended to be limiting in terms of the possible construction solutions which can be adopted by the present invention. By way of example, FIGS. 5A and 5B show a different and more general construction solution of the prosthesis 10 according to the present invention. FIG. 5A is a plan view of the two separate components 12, 14, setting out how the annular element 12 and the central member 14 may have geometries which are different from each other and both not necessarily being circular. The annular element 12 may have, as illustrated on the left in FIG. 5A, a substantially "D"-like shape which is very similar to the anatomical shape of the annulus of an intra-ventricular valve V and is therefore particularly suitable for being connected thereto during the implantation method. The central member 14 may instead have a general ovalized shape, with an asymmetrical configuration of the prosthetic valve leaflets 16, which is optimized to produce the correct coaptation in the final assembled configuration. FIG. 5B shows the assembled configuration of the prosthesis 10, as results from the resilient equilibrium reached between the two components following the expansion of the central body 14, which is initially collapsed inside the annular element 12. Since this configuration of equilibrium is substantially determined during the design phase of the prosthesis 10, because the effect of the apparatus of the native valve V is at a minimum, it is also possible to configure the system of prosthetic leaflets 16 so that they are completely competent, that is to say, without any intra-prosthetic opening during closure, in the implanted, functionally stable configuration illustrated in FIG. 5B.

FIGS. 6A, 6B and 6C show a different embodiment of the present invention. FIG. 6A illustrates the separate components 12, 14 of the prosthesis 10. The annular element 12 is deformed both in terms of the dimensions, that is to say, with a greater circumferential extent, and in terms of the shape, which is circularized. FIG. 6B shows the effect of the deformation which is imposed on the annular element 12 in the final configuration of the assembled prosthesis 10, which is different in terms of shape and dimensions from the stable configuration associated with the correct operation of the prosthesis. The opening R which is produced in the aperture as a result of the lack of coaptation between the prosthetic valve leaflets 16 is responsible for the intra-prosthetic backward flow, making the prosthesis 10 incompetent. If the deformation applied to the annular element 12 is temporary and reversible, according to the principles of the invention described above, with a transient time period which is determined by the rate of bio-erosion of the fixing component of the deformed configuration, the prosthesis 10 recovers the stable configuration thereof for normal operation with smaller radial dimensions and correct coaptation between the prosthetic valve leaflets 16. In this case, therefore, the prosthesis 10 is also capable both of producing a contraction and remodelling the annulus of the native intraventricular valve V and of gradually eliminating the valve incompetence by progressively increasing the haemodynamic load undergone by the ventricle.

Figure 7A:
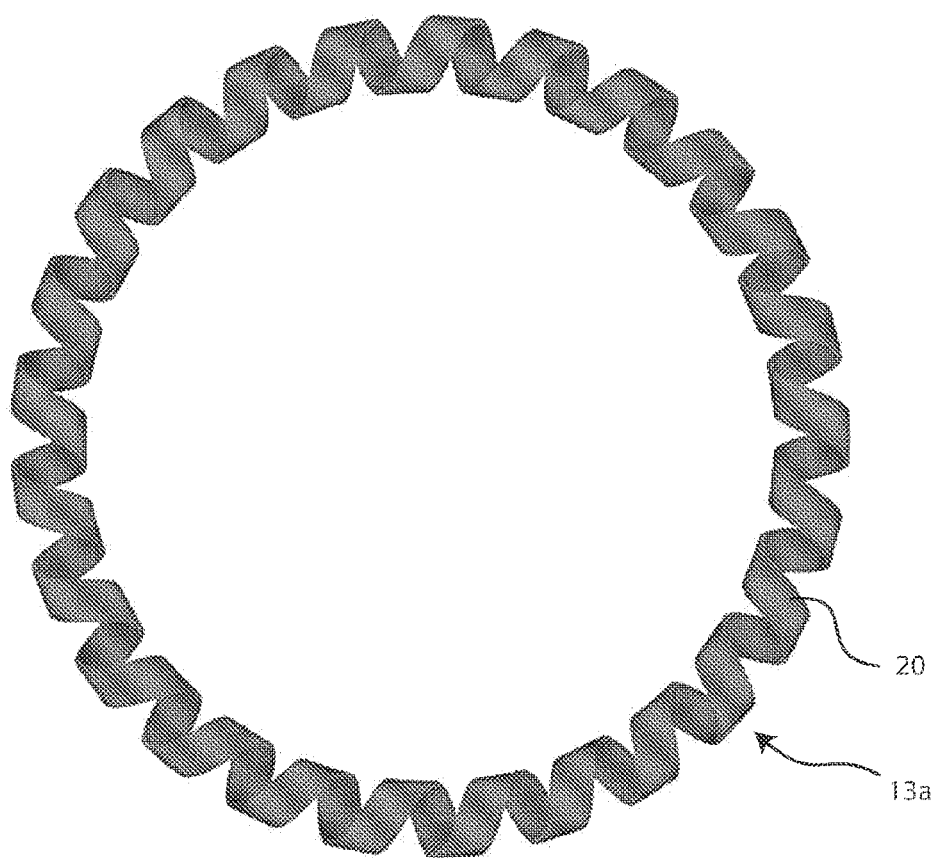
FIGS. 7A and 7B show an example of a construction solution of the core of the annular element in accordance with an embodiment of the invention which allows a deformation thereof both in terms of an increase in the longitudinal extent and in terms of a variation in shape.
Figure 7B:
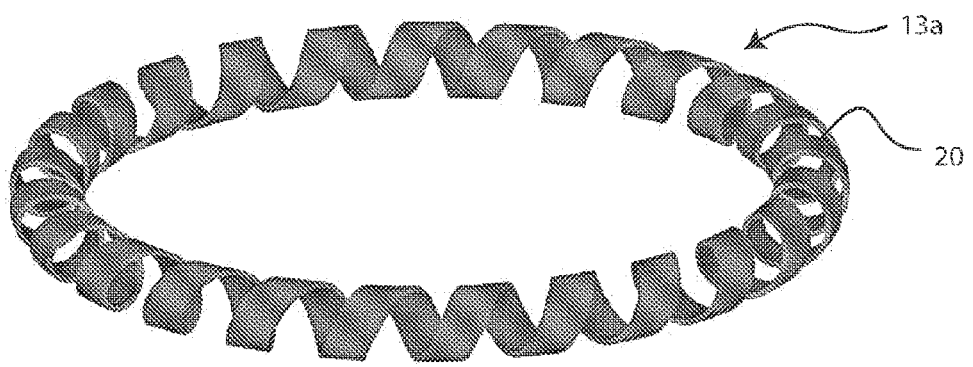

FIG. 7A and FIG. 7B show according to two different perspective views, for a better understanding of the drawing, a schematic illustration of one possible geometry of the core of the annular element in accordance with an embodiment of the invention. The core is substantially produced in a three-dimensional helical shape. A similar geometry can be obtained using a metal thread, which is pre-formed and optionally connected to the ends thereof for greater stability of the structure, or on the basis of a curved tube so as to form a closed figure, optionally with the mutually welded head ends, and in which the helical geometry is produced by cutting the wall in a suitable manner, for example, by laser cutting. The material from which the core is composed may generally be a metal or a metal alloy, for example, a titanium alloy. In particular, for devices in the field of transcatheter technologies in humans there is advantageously used nickel/titanium alloy, which is commercially known as Nitinol, as a result of the super-resilient property thereof, which allows great deformations while remaining within the range of resilience of the material, as well as for the biocompatibility thereof. As a result of the axial extensibility and the flexional deformability, the structure shown in FIG. 7 may be temporarily deformed both in terms of expansion, that is to say, increase of the axial length, and in terms of modification of the shape, advantageously filling the cavity between the contiguous helixes with a bio-absorbable or bio-erodible material according to the technique already described above.

Figure 8A:
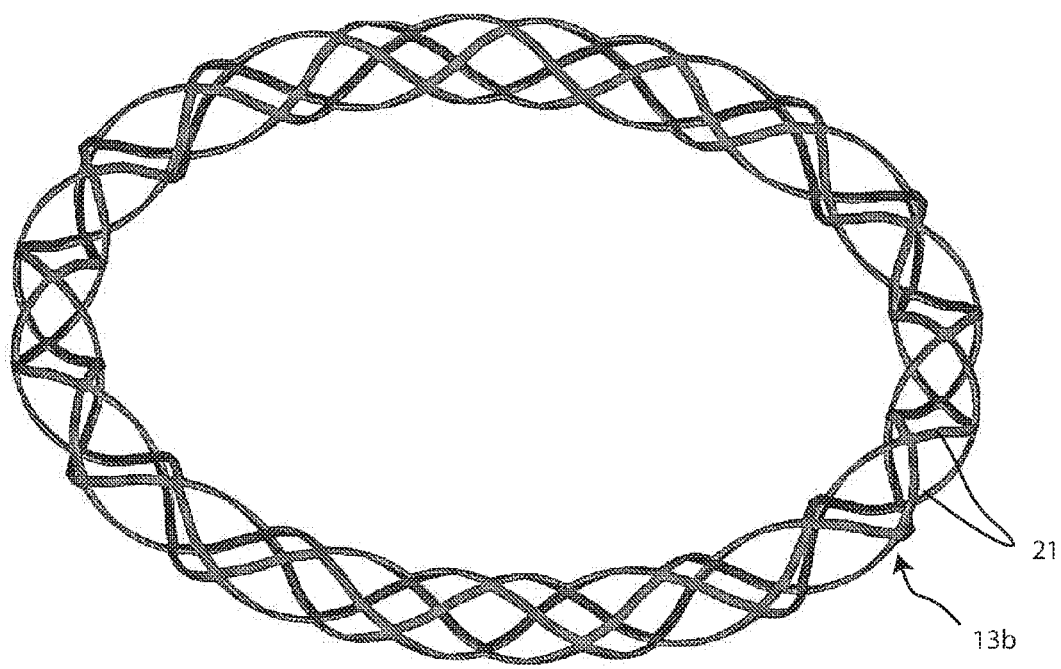
FIGS. 8A and 8B show a different construction solution of the core of the annular element in accordance with an embodiment of the invention which also allows a deformation thereof both in terms of an increase in the longitudinal extent and in terms of a variation in shape.
Figure 8B:
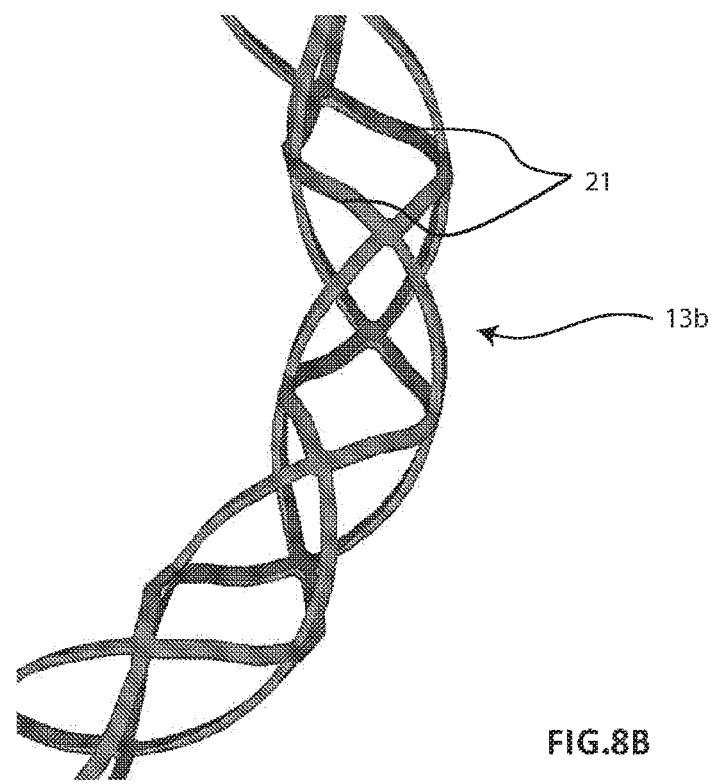

FIG. 8A and FIG. 8B illustrate another version of the core of the annular element in accordance with a different embodiment of the invention. FIG. 8A shows the core as a whole while FIG. 8B shows the detail of a portion thereof. In the construction solution shown here, the core is substantially constituted by a meshed toroidal structure. In this case, the structure may also be constructed both by means of a fabric of interwoven metal threads and by starting from a tube bent so as to form a ring, which is optionally but not necessarily closed, on the wall of which there are produced suitable openings by means of laser cutting. This last method is particularly advantageous, allowing variation as desired of the thicknesses of the arms of the mesh, as well as the dimensions, the shape and the position of the various openings formed in the wall of the tubular element. In this manner, there is provided a great freedom of configuration in order to freely adjust the resilient return of the core and therefore of the annular element in accordance with the requirements of the project. Simply by way of example, the resilient return of the core may be varied in accordance with the position, it being possible to construct regions which are more rigid and regions which are more flexible, or there can be obtained anisotropic behaviour of the structure both as a whole and only locally, which allows, for example, provision of a flexible core for deformations inside the plane but extremely rigid with respect to deformations outside the plane.

The materials which can be used are obviously the same as the construction solution described above.

Independently of the resilient characteristics which are conferred thereon, the meshed structure described in FIG. 8 affords the possibility similarly to the structure in FIG. 7 of increasing the axial extent thereof, of being deformed in accordance with different shapes with respect to the initial shape, and having both deformations superimposed.

According to an embodiment of the present invention, the deformed configuration may be fixed for a predetermined period of time by means of co-moulding of bio-erodible or biodegradable material above the suitably deformed core, for example, inside a mould, in order to produce a covering which maintains the distorting effect on the structure of the core. The co-moulding may involve all the core or also only limited portions of the core, in accordance with the particular deformation which it is desirable to achieve, or the resilient characteristics which it is desirable to preserve in the core including in the deformed configuration.

Figure 9A:
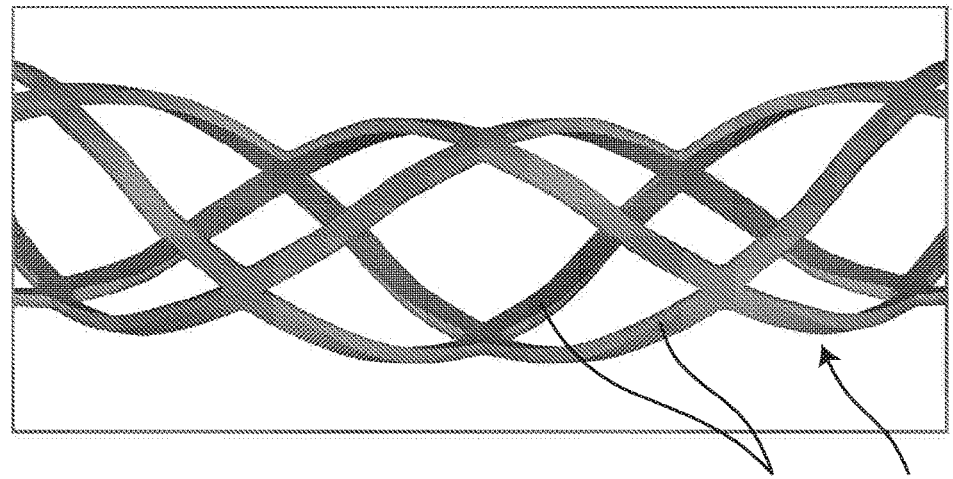
FIGS. 9A and 9B describe a technique for fixing the deformed configuration of the core of the annular element by means of blocks of bio-erodible material which are forcibly inserted in the meshed structure.
Figure 9B:
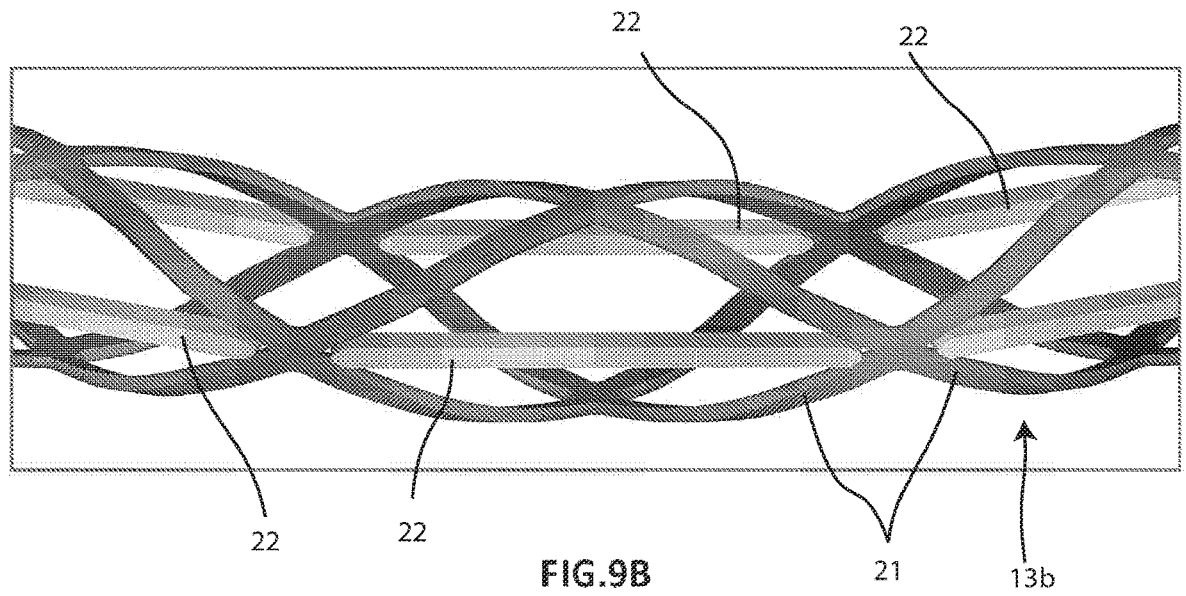

Another construction method, which is illustrated in FIG. 9A and FIG. 9B, provides for the use of inserts, such as wedges or blocks of bio-erodible material which are suitably shaped and dimensioned and which are forcibly inserted in the openings present in the mesh. In particular, FIG. 9A shows, as a reference for the following Figure, a non-deformed portion of the structure of the core described in FIG. 8. FIG. 9B shows, by way of non-limiting example of the general nature of the invention, how blocks of bio-erodible material which are suitably overdimensioned are capable of fixing a deformed configuration if forced inside the openings of the mesh of the structure of FIG. 9A. Assuming the more general case, in which the openings of the mesh have different dimensions from each other, if the criterion of over-dimensioning of each block as a function of the dimensions of the opening inside which it is forced is kept constant over the whole structure, the effect which is obtained is a homothetic expansion thereof. In other words, if the percentage of interference between the block and the opening is kept constant independently of the position on the structure, there is generally obtained the effect of increasing the axial extent of the structure without a substantial deformation of shape thereof, as indicated in FIG. 9B. If, however, the percentage of interference varies in accordance with the position, there is also obtained a variation of shape of the ring. For example, if the percentage of interference is greater for the openings in the internal face with respect to that in the external face, the radius of curvature of the axis of the structure increases (straightening effect). If, on the other hand, the percentage of interference is greater for the openings in the external face, the radius of curvature of the axis decreases (bending effect). It is evident that, by way of an application example, by applying a straightening effect (percentage of interference greater in the internal face) to two diametrically opposed portions and a bending effect (percentage of interference greater in the external face) to two diametrically opposed portions which are also orthogonal to the preceding ones, there is obtained the ovalization of a core which is initially circular or, as a specific case, the circularization of a core which is initially oval. It is also evident that it is possible to obtain only the deformation of the geometry of the core without increasing the axial extent thereof, producing the straightening effect or the bending effect by means of insertion of blocks in a single face of the structure rather than in both.

In light of the multiplicity of the possible positions of the openings in a meshed core similar to the one illustrated in FIG. 8, it may be immediately understood how extensive and varied is the range of deformations of the structure which can be obtained by means of the forced insertion of blocks or wedges of bio-erodible material which is suitably shaped and dimensioned. With the deformation being imposed in the resilient range, optionally with the use of super-resilient alloys such as Nitinol, the degradation which occurs in the human physiological field of the material from which the blocks are produced leads over time to the disappearance of the distorting effect and the recovery of the original geometric and mechanical characteristics of the core and therefore of the annular element.

Figure 10A:
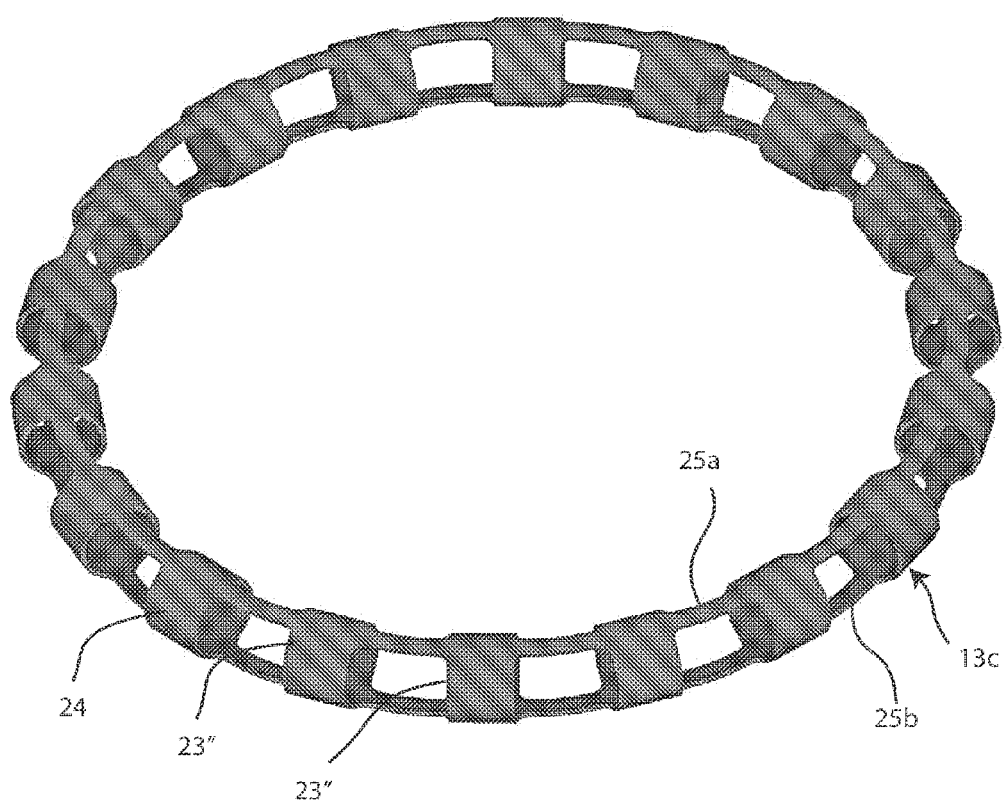
FIGS. 10A and 10B show a different construction solution of the core of the annular element in accordance with an embodiment of the invention which allows only the deformation in terms of variation of shape, being a longitudinally inextensible geometry.
Figure 10B:
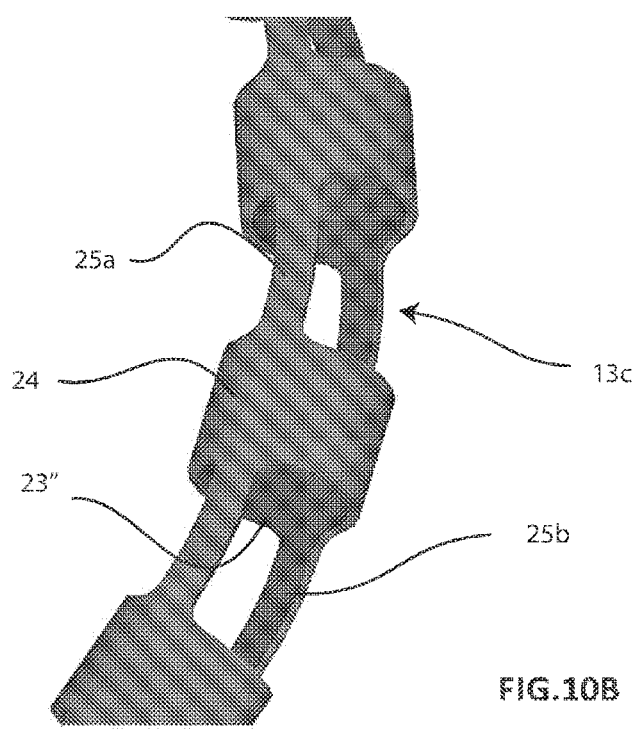
Figure 11:
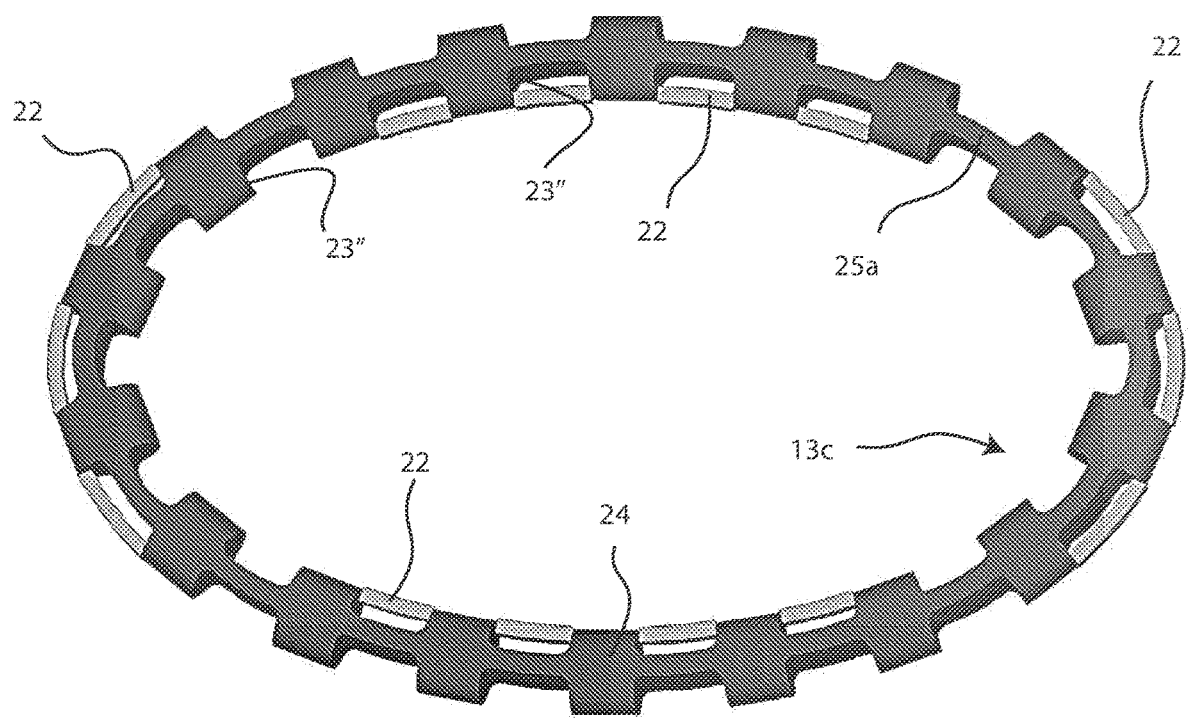
FIG. 11 describes a technique for fixing the deformed configuration of the core of the annular element by means of blocks of bio-erodible material which are forcibly inserted in some openings of the structure.

FIG. 10A and FIG. 10B show another version of the core of the annular element, in accordance with a different embodiment of the invention. The structure illustrated in FIG. 10A in its entirety and in FIG. 10B in detail for greater clarity of the configuration of the structure differs in terms of function from the one shown in FIG. 7 and in FIG. 8 because it is substantially inextensible longitudinally but only geometrically deformable. In fact, notwithstanding the large number of openings which are also formed in this configuration in the wall of the tube and which make it flexible, the presence of at least one continuous ring which joins the various sub-elements of the structure makes the structure inextensible in terms of axial extent. The presence in the structure of a single continuous ring allows deformations of the core in three-dimensional space. However, the presence of two rings which are diametrically positioned on the upper face and lower face or more generally spaced apart from each other axially as shown in FIG. 10, limits the degree of deformability of the structure in the plane. Therefore, this construction solution which may be necessary if the absolute non-extensibility of the annular element is required during the normal operating mode of the implanted prosthetic system, allows a deformed but non-expanded configuration. The geometric deformation may be temporarily fixed by means of surrounding the core, or only portions thereof, inside a covering of bio-erodible material, or by means of insertion of suitable spacers or blocks, which are produced from the same bio-erodible material and which are forced inside the openings of the structure. Merely by way of example, without wishing to limit the general nature of the invention, FIG. 11 shows the variation of shape, from circular to oval, imposed on the structure described in FIG. 10 by means of the forced insertion of blocks of bio-erodible material in some specific openings of the structure, which are selected in accordance with the desired modification to the local radius of curvature of the axis of the structure.

Figure 12A:
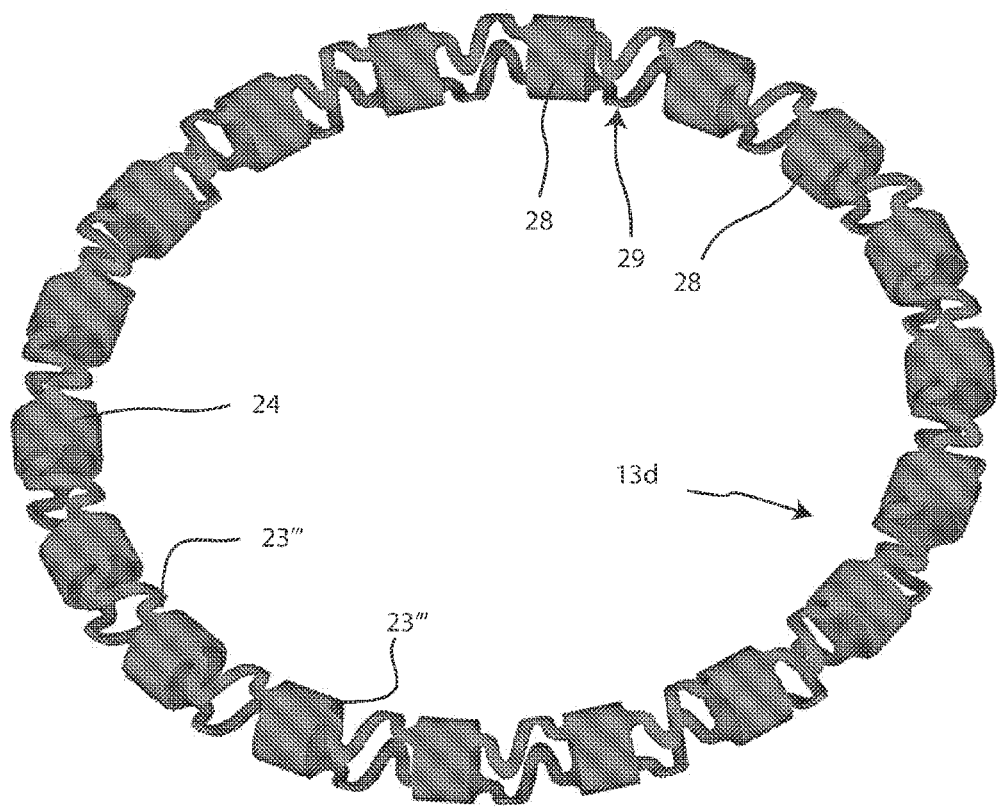
FIGS. 12A and 12B show a different construction solution of the core of the annular element in accordance with an embodiment of the invention which illustrates a variant with respect to the solution described in FIGS. 10A and 10B in order also to allow the deformation of the core in terms of longitudinal extension.
Figure 12B:
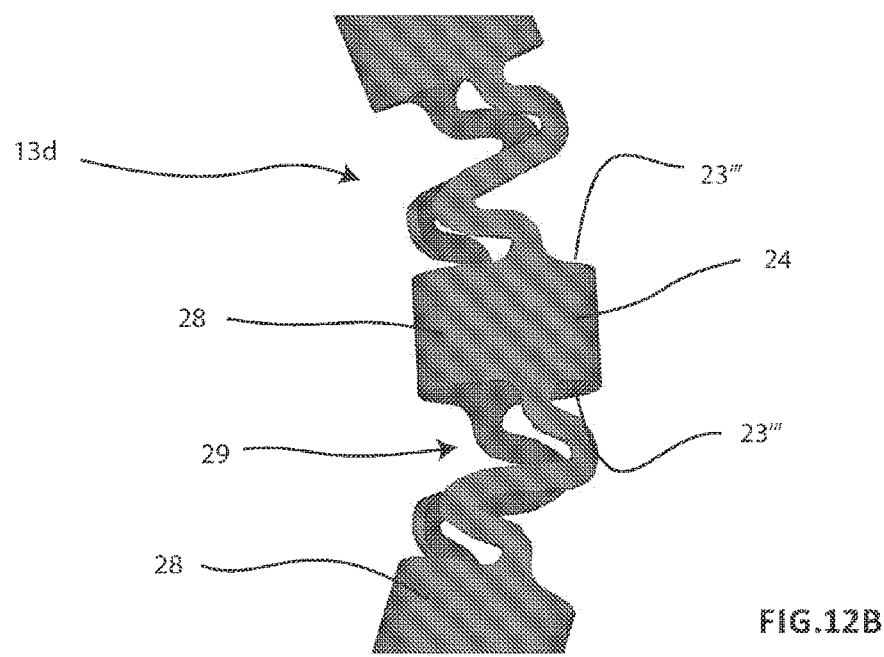

FIG. 12A and FIG. 12B show a variant of the configuration of the core of the annular element which is described in FIG. 10 which also again introduces the possibility of deforming the structure in a longitudinal direction, increasing the circumferential extent thereof, in addition to varying the shape thereof. In general, the introduction of deformable and extensible elements as constituting portions of the rings which characterize the configuration of FIG. 10 also allows the extension thereof in the axial direction. In the construction solution described in FIG. 12, the introduction of "S"-shaped elements, as clearly illustrated in FIG. 12B, introduces the additional degree of freedom given by the possibility of a dilation in the direction for increasing the circumferential extent of the core.

Figure 13A:
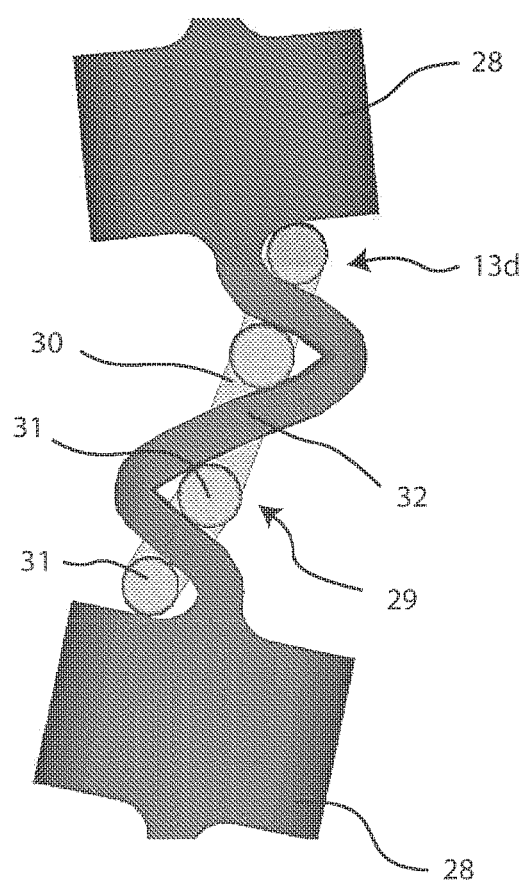
FIGS. 13A and 13B describe a technique for fixing the deformed configuration of the core of the annular element by means of inserts of bio-erodible material which are forcibly connected in the structure of the core.
Figure 13B:
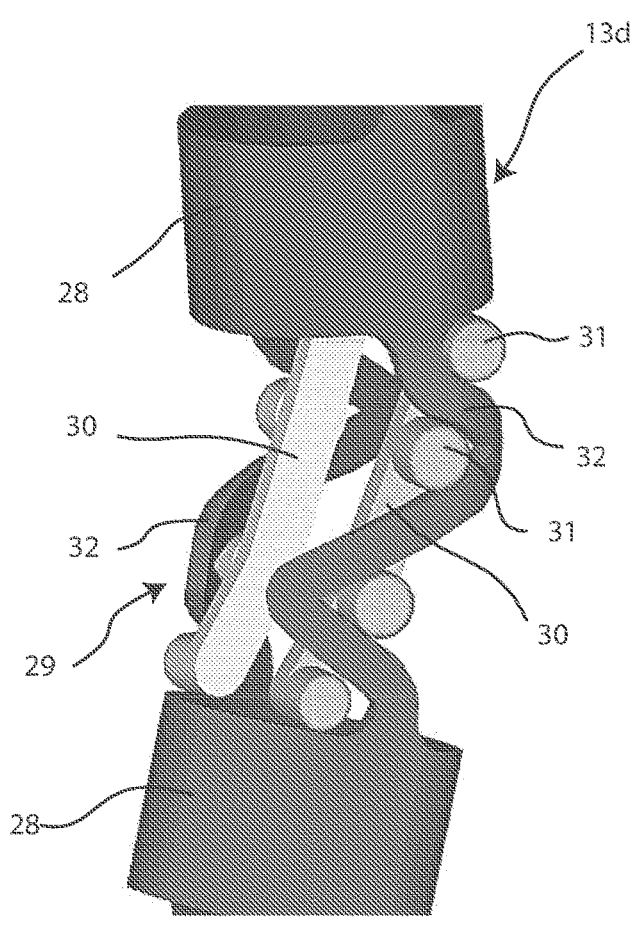

In the case of the construction solution described in FIG. 12, the deformed configuration may also be temporarily fixed by means of co-moulding bio-erodible material only in some suitably selected portions of the core, or by means of blocks and wedges which are produced from the same bio-erodible material and which are suitably dimensioned and forcibly introduced inside the openings formed in the wall of the initial toroidal structure. In addition, the construction solution in FIG. 12 allows any deformed configuration also to be blocked only by interfering, with a bio-erodible material, with the geometry of the "S"-like connection. As an example of a non-limiting construction solution of the general nature of the invention, FIG. 13A and FIG. 13B show in accordance with different perspectives for greater clarity of exposition, inserts of bio-erodible material which are provided with pins which are dimensioned and spaced apart so as to be able to be embedded in a forced manner between the arms of the "S"-like portion which joins the various sub-elements of the structure, suitably modifying the geometry thereof. The modification of the geometry brought about by the block may have both a component of dilation, in the case in which the increase of the spacing is produced between the ends of the "S"-like portion, and a component of modification of the shape, in the case in which the variation of the equivalent radius of curvature of the portion is forced. The first action therefore has the effect of increasing the total circumferential extent of the structure while the second action has the effect of modifying the shape thereof. With regard to this last aspect, it should be emphasized that the anti-symmetry of the "S"-like shape allows both an increase and a decrease of the equivalent radius of curvature in accordance with which pair of arms is spaced apart to the greater extent. The effect of increasing the circumferential extent and the distorting effect of the shape are substantially independent of each other in the sense that the whole of each one can be imposed in an autonomous and non-correlated manner on the whole of the other one.

Finally, in the context of the transcatheter technologies, this last construction solution appears to be particularly advantageous because the pins generate a local constraint of the unilateral type, as a result of which additional deformations of the structure, for example, for making the profile of the component compatible with the assembly thereof on a release catheter, are also possible in the presence of the inserts.

Naturally, the principle of the invention remaining the same, the forms of embodiment and details of construction may be varied widely with respect to those described and illustrated, without thereby departing from the scope of the present invention.

The invention claimed is:
1. A method for producing a prosthesis for a native cardiac valve, comprising the steps of:
providing a prosthesis for a cardiac valve comprising prosthetic leaflets which are intended to functionally replace the native leaflets of a cardiac valve following the implantation of the cardiac prosthesis, and a prosthetic member on which there are mounted the prosthetic leaflets and which is intended to take up a stable, predetermined functional configuration in which the prosthetic member and the prosthetic leaflets reproduce a functionally correct configuration for physiological replacement of the native cardiac valve, and
preconfiguring the prosthetic member to be fixed in position in an altered, temporary functional configuration that temporarily physiologically replaces the native cardiac valve, in which the prosthetic member is allowed to expand to a greater extent and/or to expand to a greater extent in accordance with a different geometry from that provided for in said stable, predetermined functional configuration, and so as to move gradually during use from the altered, temporary functional configuration to the stable, predetermined functional configuration that stably physiologically replaces the native cardiac valve.
2. The method according to claim 1, wherein the prosthetic member is resiliently deformed geometrically and fixed in the altered, temporary functional configuration by retention members which are gradually dissolvable during use.

3. A method for producing a prosthesis for a native cardiac valve, comprising the steps of:

provicing a prosthesis for a cardiac valve comprising prosthetic leaflets which are intended to functionally replace the native leaflets of a cardiac valve following the implantation of the cardiac prosthesis, and a prosthetic member on which there are mounted the prosthetic leaflets and which is intended to take up a stable, predetermined functional configuration in which the prosthetic member and the prosthetic leaflets reproduce a functionally correct configuration for physiological replacement of the native cardiac valve, and preconfiguring the prosthetic member to be fixed in position in an altered, temporary functional configuration that temporarily physiologically replaces the native cardiac valve, in which the prosthetic member is allowed to expand to a greater extent from that provided for in said stable, predetermined functional configuration, and/or in accordance with a different geometry, moving from one shape to another shape while a perimeter thereof is not reduced in respect to that provided for in said stable, predetermined functional configuration, and so as to move gradually during use from the altered, temporary functional configuration to the stable, predetermined functional configuration that stably physiologically replaces the native cardiac valve.

* * * * *